United States Patent
Maeda et al.

(10) Patent No.: US 10,085,708 B2
(45) Date of Patent: Oct. 2, 2018

(54) MEDICAL IMAGE PROCESSING APPARATUS, MEDICAL IMAGE DIAGNOSTIC APPARATUS, AND IMAGE PROCESSING METHOD

(71) Applicant: Toshiba Medical Systems Corporation, Otawara-shi (JP)

(72) Inventors: Tatsuo Maeda, Nasushiobara (JP); Laurent Lessieux, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/591,536

(22) Filed: May 10, 2017

(65) Prior Publication Data

US 2017/0325772 A1 Nov. 16, 2017

(30) Foreign Application Priority Data

May 11, 2016 (JP) .................................. 2016-095163
May 2, 2017 (JP) .................................. 2017-091509

(51) Int. Cl.

| G06K 9/00 | (2006.01) |
| A61B 6/00 | (2006.01) |
| G06T 7/11 | (2017.01) |
| A61B 5/055 | (2006.01) |
| A61B 6/03 | (2006.01) |
| G06T 7/00 | (2017.01) |

(Continued)

(52) U.S. Cl.
CPC ............ *A61B 6/5217* (2013.01); *A61B 5/055* (2013.01); *A61B 6/032* (2013.01); *A61B 6/463* (2013.01); *A61B 6/505* (2013.01); *G06T 7/0012* (2013.01); *G06T 7/11* (2017.01); *G06T 11/001* (2013.01); *G06T 11/60* (2013.01); *G06T 2207/10024* (2013.01); *G06T 2207/10081* (2013.01); *G06T 2207/10088* (2013.01); *G06T 2207/30008* (2013.01)

(58) Field of Classification Search
CPC ............ G06T 7/11; G06T 2207/10088; G06T 2207/10081; G06T 2207/10024; G06T 11/60; G06T 11/001; G06T 7/0012; G06T 2207/30008; A61B 6/5217; A61B 6/505; A61B 6/463; A61B 6/032; A61B 5/055
USPC ......................................................... 382/128
See application file for complete search history.

(56) References Cited

U.S. PATENT DOCUMENTS

2016/0143699 A1* 5/2016 Tanji ...................... A61B 34/20
600/431

FOREIGN PATENT DOCUMENTS

JP 2000-342558 * 12/2000 ............... G06T 7/00

* cited by examiner

*Primary Examiner* — Gregory F Cunningham
(74) *Attorney, Agent, or Firm* — Oblon, McClelland, Maier & Neustadt, L.L.P.

(57) ABSTRACT

A medical image processing apparatus includes processing circuitry and a display. The processing circuitry acquires object volume data including a bone fracture region acquired from a subject and target volume data acquired based on a healthy bone region corresponding to the bone fracture region. The processing circuitry extracts a plurality of fragment regions from the object volume data. The processing circuitry arranges the plurality of extracted fragment regions in the object volume data based on shapes of the plurality of fragment regions and a shape of a bone region included in the target volume data. The display displays an image based on the object volume data in which the fragment regions are arranged.

17 Claims, 6 Drawing Sheets

Bone suffering disease    Healthy bone having undergone mirror image reversal

(51) Int. Cl.
*G06T 11/00* (2006.01)
*G06T 11/60* (2006.01)

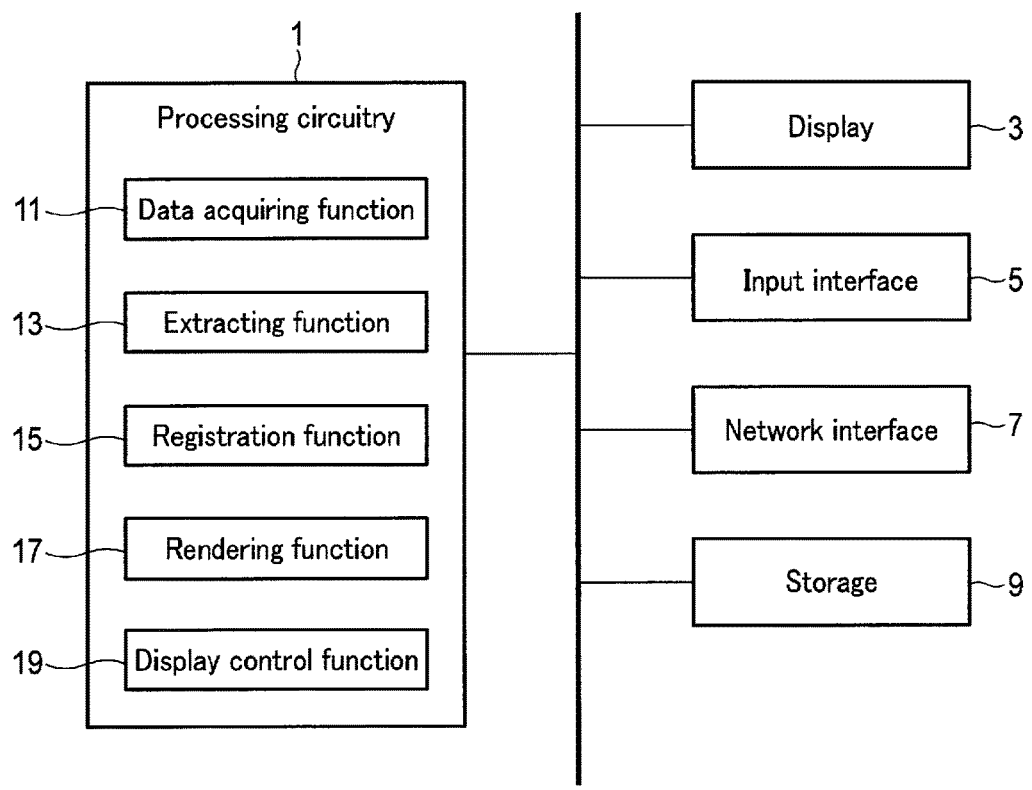
F I G. 1

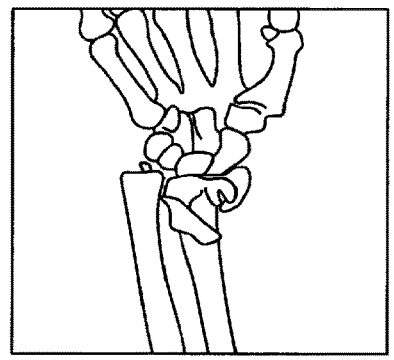
F I G. 3
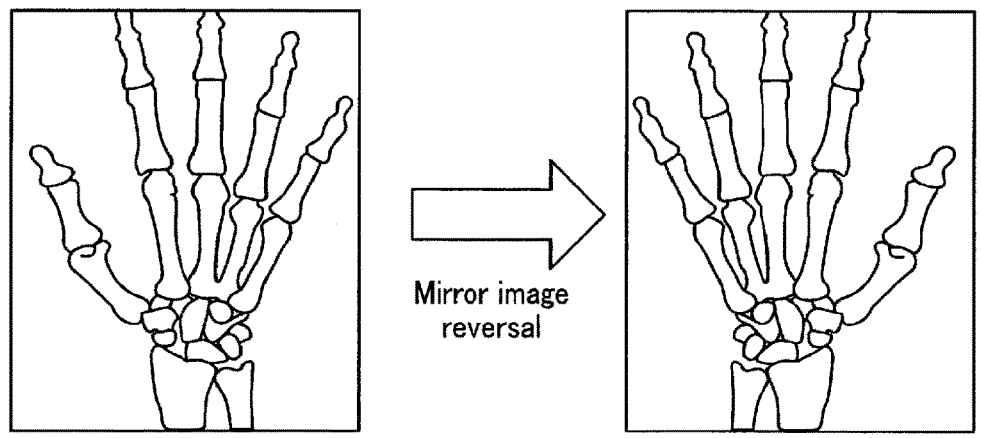
F I G. 4

Bone suffering disease | Healthy bone having undergone mirror image reversal

MEDICAL IMAGE PROCESSING APPARATUS, MEDICAL IMAGE DIAGNOSTIC APPARATUS, AND IMAGE PROCESSING METHOD

CROSS-REFERENCE TO RELATED APPLICATIONS

This application is based upon and claims the benefit of priority from the prior Japanese Patent Applications No. 2016-095163, filed May 11, 2016 and No. 2017-91509, filed May 2, 2017, the entire contents of both which are incorporated herein by reference.

FIELD

Embodiments described herein relate generally to a medical image processing apparatus, a medical image diagnostic apparatus, and an image processing method.

BACKGROUND

When treating a bone fracture, an image with which the reduced state of the bone fracture can be grasped is requested. A conventional medical image processing apparatus responds to this request by using, for example, an image in which a healthy bone is reversed and displayed. However, for the image in which the healthy bone is reversed and displayed, an operator such as a doctor needs to consider where the broken bone is reduced, thereby placing a burden on the operator.

BRIEF DESCRIPTION OF THE DRAWINGS

FIG. 1 is a block diagram showing the arrangement of a medical image processing apparatus according to an embodiment;
FIG. 3 is a view showing a surface volume rendering image which includes a bone fracture region and is generated by processing circuitry shown in FIG. 1;
FIG. 4 is a view showing a target surface volume rendering image which is generated by the processing circuitry shown in FIG. 1.

DETAILED DESCRIPTION

Figure 2:
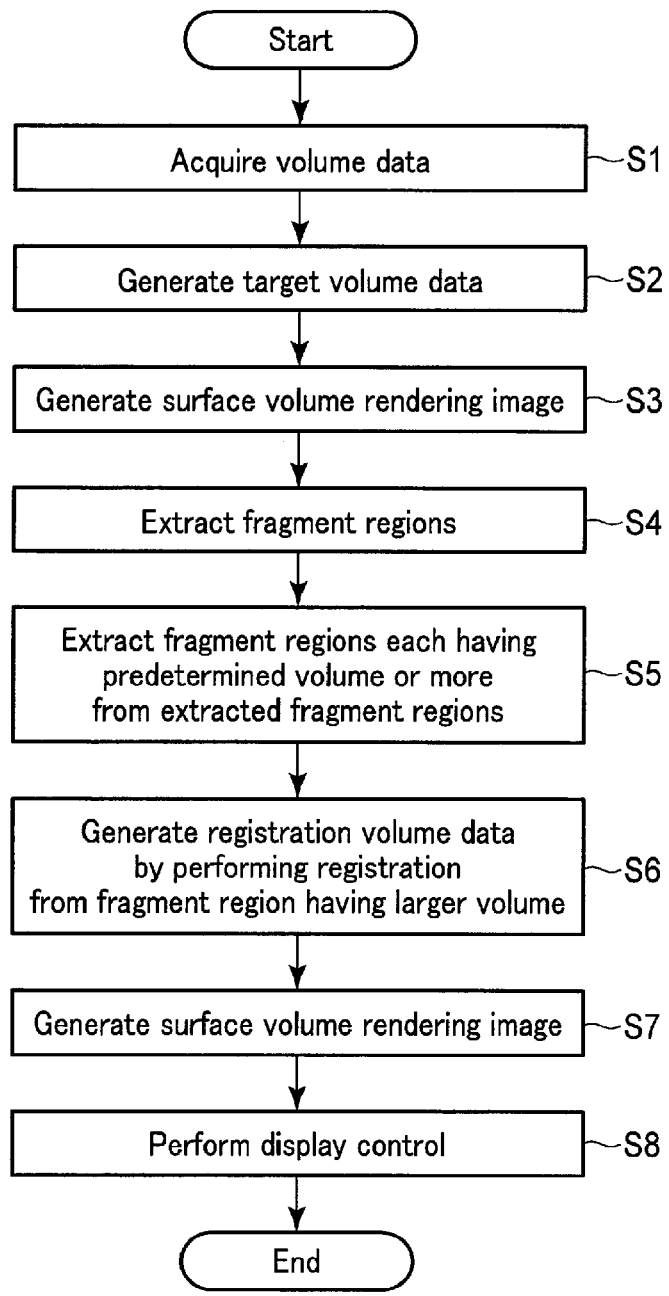
FIG. 2 is a flowchart illustrating the procedure of image processing performed by the medical image processing apparatus according to the embodiment.

In general, according to one embodiment, a medical image processing apparatus includes processing circuitry and a display. The processing circuitry acquires object volume data including a bone fracture region acquired from a subject and target volume data acquired based on a healthy bone region corresponding to the bone fracture region. The processing circuitry extracts a plurality of fragment regions from the object volume data. The processing circuitry arranges the plurality of extracted fragment regions in the object volume data based on shapes of the plurality of fragment regions and a shape of a bone region included in the target volume data. The display displays an image based on the object volume data in which the fragment regions are arranged.

The embodiment will be described below with reference to the accompanying drawings.

A medical image processing apparatus according to this embodiment is any computer capable of performing image processing for a medical image. For example, as the medical image processing apparatus according to this embodiment, a workstation, a Picture Archiving Communication System (PACS) viewer, or the like may be used. The medical image processing apparatus according to this embodiment may be incorporated in a modality such as an X-ray computed tomography apparatus, X-ray diagnostic apparatus, or magnetic resonance imaging apparatus.

FIG. 1 is a block diagram showing an example of the arrangement of the medical image processing apparatus according to this embodiment. The medical image processing apparatus shown in FIG. 1 includes processing circuitry 1, a display 3, an input interface 5, a network interface 7, and a storage 9. The processing circuitry 1, display 3, input interface 5, network interface 7, and storage 9 are communicably connected to each other via, for example, a bus.

The processing circuitry 1 is a processor serving as a center function of the medical image processing apparatus. The processing circuitry 1 executes an image processing program stored in the storage 9 or the like, thereby implementing a function corresponding to the program.

The display 3 includes, for example, a display interface and a display device. As the display device, for example, a CRT display, a liquid crystal display, an organic EL display, an LED display, a plasma display, or another arbitrary display known in this technical field is appropriately usable. The display interface converts data representing a display object into a video signal. The display device displays the video signal representing the display object.

The input interface 5 is implemented by, for example, a mouse, a keyboard, a touchpad whose operation surface is touched to input an instruction, and the like. The input interface 5 accepts various instructions from an operator. The input interface 5 is connected to the processing circuitry 1 via, for example, the bus, and converts an operation instruction input by the operator into an electrical signal and outputs it to the processing circuitry 1. Note that in this specification, the input interface 5 is not limited to that including physical operation parts such as a mouse and keyboard. For example, an example of the input interface 5 is electrical signal processing circuitry for receiving an electrical signal corresponding to an operation instruction input from an external input device provided separately from the medical image processing apparatus, and outputting the electrical signal to the processing circuitry 1.

The network interface 7 performs data communication with an external apparatus such as a PACS server and a modality connected via a network (not shown) or the like. Any standard may be adopted as the standard of communication with the external apparatus. An example of the standard is Digital Imaging and Communication in Medicine (DICOM).

The storage 9 is a storage device such as a Hard Disk Drive (HDD), a Solid State Drive (SSD), and an integrated circuit storage device for storing various kinds of information. The storage 9 may be, for example, a driving device for reading/writing various kinds of information from/in a portable storage medium such as a CD-ROM drive, DVD drive, and flash memory. For example, the storage 9 stores data (to be referred to as volume data hereinafter) of a three-dimensional medical image generated by the above-described modality with respect to a subject such as a patient according to this embodiment. The medical image according to this embodiment includes an image region (to be referred to as a bone fracture region hereinafter) associated with a bone suffering a disease such as a bone fracture or an image region (to be referred to as a healthy bone region hereinafter) associated with a healthy bone corresponding to the bone suffering the disease. The healthy bone corresponding to the bone suffering the disease indicates a bone which is laterally opposite to the bone suffering the disease. The storage 9 stores the image processing program and the like according to this embodiment.

The processing circuitry 1 according to this embodiment implements registration of image regions (to be referred to as fragment regions hereinafter) associated with a plurality of fragments included in the bone fracture region and the like by executing the image processing program according to this embodiment. Note that in this embodiment, the fragments include a bone which bends but is partially connected, in addition to a disconnected bone. More specifically, the processing circuitry 1 has a data acquiring function 11, an extracting function 13, a registration function 15, a rendering function 17, and a display control function 19 by executing the image processing program.

By executing the data acquiring function 11, the processing circuitry 1 acquires, from the storage 9, object volume data including the bone fracture region and volume data including the healthy bone region. The processing circuitry 1 generates target volume data using the volume data including the healthy bone region. The target volume data is data including a bone region for performing registration of the fragment regions included in the bone fracture region. For example, the processing circuitry 1 generates target volume data, as follows. That is, the processing circuitry 1 extracts the healthy bone region from the volume data including the healthy bone region. To extract the healthy bone region, for example, a method of performing, when an arbitrary position in the volume data is selected using the input interface 5, segmentation by setting the selected position as the center, and setting the segmented bone as the healthy bone region is used. The processing circuitry 1 generates target volume data by performing mirror image reversal processing for data about the extracted healthy bone region. Note that the mirror image reversal processing includes horizontal reversal processing and vertical reversal processing.

By executing the extracting function 13, the processing circuitry 1 extracts, from the object volume data including the bone fracture region, fragment regions each having a preset size or more. In this embodiment, as a parameter representing the size, for example, the volume or surface area of the fragment region is used. Note that a case in which the volume is used as the parameter representing the size is used will be exemplified below.

By executing the registration function 15, the processing circuitry 1 registers each of the extracted fragment regions with a portion having a closest shape in the bone region included in the target volume data, in descending order of volumes. The processing circuitry 1 generates registration volume data by performing registration of the extracted fragment regions based on the target volume data.

By executing the rendering function 17, the processing circuitry 1 executes rendering processing for various volume data. As the rendering processing according to this embodiment, any processing for generating a two-dimensional display image from a three-dimensional image, such as volume rendering, surface volume rendering, image value projection processing, Multi-Planer Reconstruction (MPR) processing, and Curved MPR (CPR) processing is included.

By executing the display control function 19, the processing circuitry 1 controls the display 3 to display a rendering image generated by the rendering processing.

Note that the data acquiring function 11, extracting function 13, registration function 15, rendering function 17, and display control function 19 are modules forming the image processing program according to this embodiment. This embodiment, however, is not limited to this. For example, the processing circuitry 1 may include dedicated hardware circuitry for implementing the data acquiring function 11, that for implementing the extracting function 13, that for implementing the registration function 15, that for implementing the rendering function 17, and that for implementing the display control function 19. The processing circuitry 1 may be implemented by an Application Specific Integrated Circuit (ASIC), Field Programmable Logic Device (FPGA), Complex Programmable Logic Device (CPLD), or Simple Programmable Logic Device (SPLD), which incorporates the dedicated hardware circuitry.

FIG. 2 is a flowchart illustrating the typical procedure of the image processing performed by the medical image processing apparatus according to this embodiment. The medical image according to this embodiment is assumed to be a three-dimensional CT image generated by the X-ray computed tomography apparatus. The CT image is generated when the X-ray computed tomography apparatus CT-scans a portion including a broken bone and a portion including a healthy bone corresponding to the broken bone. Assume that in the CT image, the bone fracture region or the healthy bone region is depicted. Assume also that, for example, the CT image is transmitted from the X-ray computed tomography apparatus to the medical image processing apparatus or transmitted to the medical image processing apparatus via the PACS, and stored in the storage 9.

The operator inputs, via the input interface 5, an instruction to start the image processing according to this embodiment. Upon receiving the instruction to start the image processing, the processing circuitry 1 executes the data acquiring function 11. The processing circuitry 1 executes the data acquiring function 11 to acquire, from the storage 9, the object volume data including the bone fracture region and the volume data including the healthy bone region (step S1).

Upon acquiring the volume data including the healthy bone region, the processing circuitry 1 extracts the healthy bone region from the volume data. The processing circuitry 1 generates target volume data by performing mirror image reversal processing for data about the extracted healthy bone region (step S2).

After acquiring the object volume data including the bone fracture region and generating the target volume data, the processing circuitry 1 executes the rendering function 17. The processing circuitry 1 executes the rendering function 17 to perform rendering processing for the object volume data including the bone fracture region, thereby generating a surface volume rendering image including the bone fracture region. Furthermore, the processing circuitry 1 performs the rendering processing for the target volume data, thereby generating a surface volume rendering image which serves as a target when reducing the bone fracture (step S3). As the rendering processing, surface volume rendering processing for generating the shape of the bone is desirable.

After generating the surface volume rendering image including the bone fracture region and the target surface volume rendering image, the processing circuitry 1 may execute the display control function 19. The processing circuitry 1 executes the display control function 19 to display the surface volume rendering image including the bone fracture region and the target surface volume rendering image side by side on, for example, the display 3. Note that the processing circuitry 1 may superimpose the surface volume rendering image including the bone fracture region on the target surface volume rendering image, and display them on the display 3. FIG. 3 is a view showing the surface volume rendering image including the bone fracture region, which is generated in step S3. FIG. 3 shows, as an example, a surface volume rendering image of a left distal radius fracture. FIG. 4 is a view showing the target surface volume rendering image which is generated in step S3. FIG. 4 shows, as an example, a surface volume rendering image acquired by performing mirror image reversal processing for a healthy right hand.

Figure 5:
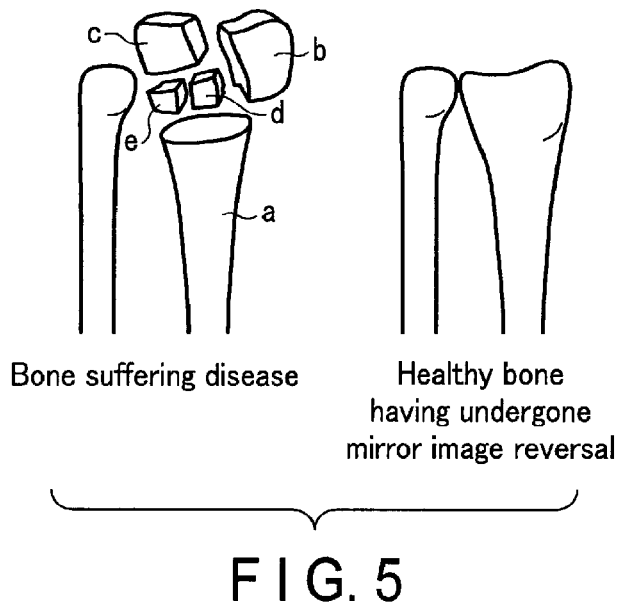
FIG. 5 is a view showing fragment regions extracted by the processing circuitry shown in FIG. 1.

After performing step S3, the processing circuitry 1 executes the extracting function 13. The processing circuitry 1 executes the extracting function 13 to perform segmentation processing for the object volume data including the bone fracture region, thereby extracting the fragment regions included in the object volume data (step S4). As the segmentation processing according to this embodiment, for example, any processing for extracting a predetermined region from volume data, such as threshold processing, region generation, and texture analysis is included. FIG. 5 is a view schematically showing the fragment regions extracted by the processing circuitry 1 in step S4. FIG. 5 exemplifies a case in which the segmentation processing is performed for the data of the left distal radius fracture to extract fragment regions a, b, c, d, and e. Note that for the sake of comparison, FIG. 5 shows a schematic view when the mirror image reversal processing is performed for the bones of the right hand including healthy bones.

Figure 6:
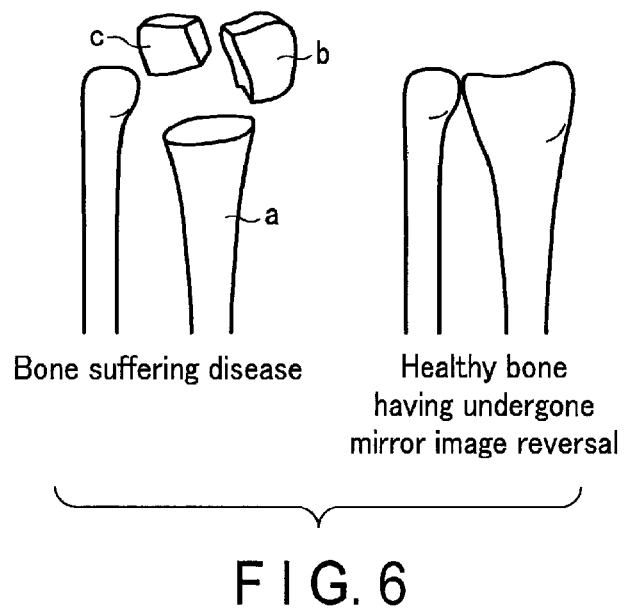
FIG. 6 is a view showing the fragment regions extracted based on their volumes by the processing circuitry shown in FIG. 1.

The processing circuitry 1 calculates the volume of each of the extracted fragment regions based on pixel values (voxel values), and compares the calculated volume with a preset threshold. The processing circuitry 1 extracts, as registration candidates, the fragment regions each having a volume exceeding the threshold (step S5). Note that the processing circuitry 1 may calculate the surface area of each of the extracted fragment regions based on pixel values (voxel values), compare the calculated surface area with a preset threshold, and then extract the fragment region as a registration candidate. FIG. 6 is a view schematically showing the fragment regions extracted in step S5. FIG. 6 exemplifies a case in which among fragment regions a, b, c, d, and e shown in FIG. 5, fragment regions d and e each having a small volume are excluded from registration candidates. Note that for the sake of comparison, FIG. 6 shows a schematic view when the mirror image reversal processing is performed for the bones of the right hand including healthy bones.

The processing circuitry 1 may execute the extracting function 13 to set a boundary portion with respect to the fragment regions extracted in step S5. In this embodiment, the boundary portion indicates a portion representing the boundary of the bone fracture in the fragment region. For example, the boundary portion is set based on the surface shape of each fragment region. The processing circuitry 1 acquires information about the surface shape of the fragment region by extending the fragment region by one pixel and subtracting the fragment region before the extension from the fragment region after the extension. The processing circuitry 1 approximates a fitting curve representing the surface shape from the acquired information, and acquires, for example, feature amounts such as inflection points for defining smoothness based on the fitting curve. The processing circuitry 1 matches the acquired feature amounts with the preset definition of a bone fracture, and detects a boundary portion in the fragment region. The definition of a bone fracture includes existence of inflection points the number of which is equal to or larger than a preset number within a predetermined range of about several mm, that is, existence of the fine three-dimensional structure of the surface.

The boundary portion in the fragment region may be detected based on exposure of a cancellous bone from the fragment surface. A bone is formed by a hard portion called a cortical bone covering the outside and a mesh portion called a cancellous bone located inside. Thus, a portion where the cancellous bone is exposed from the surface of the bone can be determined as a bone fracture portion. The processing circuitry 1 performs, for the fragment region, pattern matching processing based on a mesh pattern expressing the cancellous bone, thereby detecting the cancellous bone exposed from the fragment surface. The processing circuitry 1 sets, as a boundary portion, the portion where the cancellous bone is exposed.

After performing step S5, the processing circuitry 1 executes the registration function 15. The processing circuitry 1 executes the registration function 15 to register the position of each of the fragment regions extracted in step S5 with a predetermined portion in the bone region included in the target volume data, thereby generating registration volume data (step S6). In step S6, the processing circuitry 1 selects one of the fragment regions extracted in step S5, which has the largest volume. The processing circuitry 1 compares the selected fragment region with the predetermined portion in the bone region included in the target volume data, and calculates an evaluation value representing whether the shape of the selected fragment region is similar to that of the predetermined portion in the bone region. The processing circuitry 1 calculates, for example, the differences between a voxel value at a predetermined position of the bone region included in the target volume data and voxel values of the selected fragment region, and uses the integrated value of the difference values as an evaluation value. The processing circuitry 1 calculates the evaluation value for each portion while moving the selected fragment region within the bone region included in the target volume data. The processing circuitry 1 arranges the selected fragment region in a portion having the best calculated evaluation value. Note that if the evaluation value is calculated by integrating the difference values, a portion for which the smallest evaluation value is calculated is best.

After the registration of the selected fragment region ends, the processing circuitry 1 performs registration of the fragment region having the second largest volume. The processing circuitry 1 calculates an evaluation value for each portion while moving the selected fragment region within the bone region included in the target volume data. At this time, the portion with which the preceding fragment region has been registered is excluded from objects for which evaluation values are calculated. The processing circuitry 1 arranges the selected fragment region in a portion having the best calculated evaluation value. The processing circuitry 1 generates registration volume data by registering the fragment regions extracted in step S5 with the bone region included in the target volume data in descending order of volumes.

Figure 7:
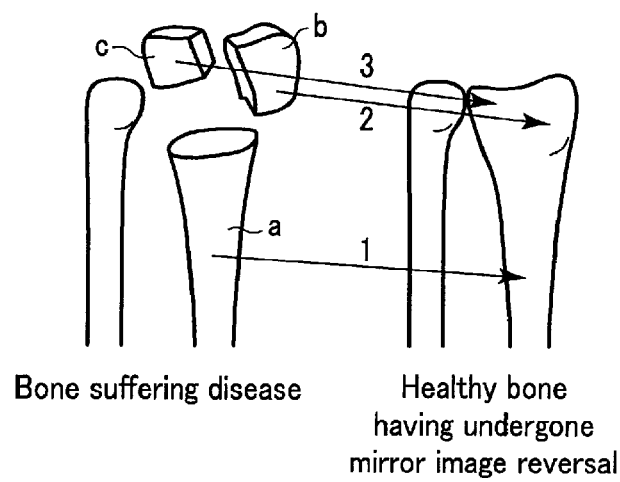
FIG. 7 is a view showing registration performed by the processing circuitry shown in FIG. 1.

If the boundary portion is set in each fragment region in step S5, the processing circuitry 1 executes, in step S6, the registration function 15 to calculate an evaluation value in consideration of whether the portion is the boundary portion. For example, the processing circuitry 1 need not use voxel values in the boundary portion to calculate an evaluation value. The processing circuitry 1 may set, for the boundary portions and the remaining portions, different weights to be used to calculate evaluation values. For example, the processing circuitry 1 sets a coefficient for voxel values in the boundary portions, which is smaller than a coefficient for voxel values in the remaining portions. The processing circuitry 1 arranges the selected fragment region in a portion having the best evaluation value calculated in consideration of the boundary portion. FIG. 7 is a view schematically showing registration performed by the processing circuitry 1 in step S6. In FIG. 7, registration with the bone region of the target volume data is performed based on the evaluation values in descending order of volumes, that is, in the order of fragment regions a, b, and c.

After generating the registration volume data, the processing circuitry 1 executes the rendering function 17. The processing circuitry 1 executes the rendering function 17 to perform rendering processing for the registration volume data, thereby generating a surface volume rendering image (step S7).

Figure 8:
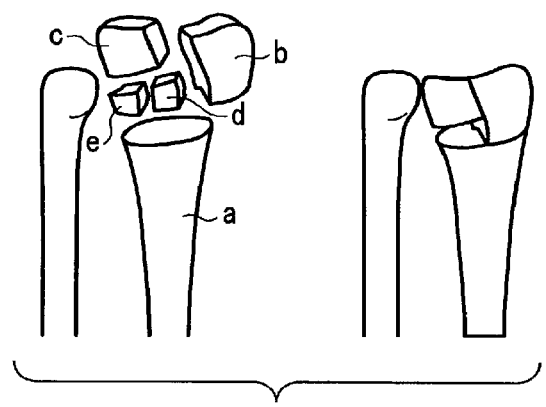
FIG. 8 is a view showing a surface volume rendering image including a bone fracture region and a surface volume rendering image after the registration.

After generating the surface volume rendering image for the registration volume data, the processing circuitry 1 executes the display control function 19. The processing circuitry 1 executes the display control function 19 to display the generated surface volume rendering image on the display 3 (step S8). At this time, the processing circuitry 1 may display the surface volume rendering image including the bone fracture region and the surface volume rendering image after the registration side by side, or superimpose and display the surface volume rendering image including the bone fracture region on the surface volume rendering image after the registration. FIG. 8 is a schematic view showing a display example of the display 3 when the surface volume rendering image including the bone fracture region and the surface volume rendering image after the registration are displayed side by side. The processing circuitry 1 may display the surface volume rendering image after the registration and the target surface volume rendering image side by side, or superimpose and display the surface volume rendering image after the registration on the target surface volume rendering image.

The processing circuitry 1 may execute the display control function 19 to process the surface volume rendering image after the registration in a display format according to a request from the operator. For example, the processing circuitry 1 may change, to a predetermined color, the color of each fragment included in the surface volume rendering image after the registration. For example, the processing circuitry 1 sets the color of at least one fragment to one of a plurality of preset colors. Note that the processing circuitry 1 may change the color of a fragment based on an instruction from the operator. This allows the operator to intuitively recognize a portion of the target bone, with which the fragment has been registered. Note that the processing circuitry 1 may switch, based on an instruction from the operator, whether to change the color arrangement.

Furthermore, for example, the processing circuitry 1 may change the opacity of at least one fragment included in the surface volume rendering image after the registration. For example, the processing circuitry 1 sets the opacity of at least one fragment to a preset level. Note that the processing circuitry 1 may change the opacity of the fragment based on an instruction from the operator. This allows the operator to confirm the state of the automatically registered fragment inside the bone. Note that the processing circuitry 1 may switch, based on an instruction from the operator, whether to change the opacity.

For example, the processing circuitry 1 may display a boundary line in a portion where fragments contact each other in the surface volume rendering image after the registration. More specifically, for example, the processing circuitry 1 detects points at which fragments contact each other in the surface volume rendering image after the registration. The processing circuitry 1 displays a boundary line in the surface volume rendering image after the registration by setting the predetermined color for the detected points. Furthermore, for example, the processing circuitry 1 acquires information about a surface included in only the surface volume rendering image after the registration by obtaining the difference between the target surface volume rendering image and the surface volume rendering image after the registration. The processing circuitry 1 displays a boundary line in the surface volume rendering image after the registration by setting the predetermined color for the acquired surface. Note that the processing circuitry 1 may switch, based on an instruction from the operator, whether to display a boundary line.

Note that in the description of FIG. 2, a case in which the processing circuitry 1 displays the surface volume rendering image on the display 3 in step S8 and then process ends has been exemplified. The present embodiment, however, is not limited to this. The processing circuitry 1 may allow the operator to manually adjust the position of the registered fragment displayed on the display 3. For example, the processing circuitry 1 executes the registration function 15 to set a state in which the operator can select the fragments included in the surface volume rendering image displayed on the display 3 in step S8. If the operator selects the fragment, and moves the selected fragment, the processing circuitry 1 updates the registration volume data based on the position after the movement. When treating the bone fracture, the bone may be regenerated more quickly by providing a gap between the fragments. It is possible to respond to such request by allowing the operator to manually adjust the position of the fragment in the surface volume rendering image. In addition, if the inside of the bone can be visually perceived by adjusting the opacity of the fragment included in the surface volume rendering image, the operator can adjust the position of the fragment which cannot be visually perceived from the surface. Note that in response to an instruction from the operator, the processing circuitry 1 may delete an instructed one of the fragments included in the surface volume rendering image after the registration.

In addition, there may be a fragment for which registration cannot be appropriately performed due to deformation of the fragment. The operator may manually perform registration of such fragment after registration of the remaining fragments ends.

Bone fractures include a complete fracture in which a bone is disconnected and an incomplete fracture in which a bone is partially connected. In the case of a complete fracture, fragments can be extracted by segmentation processing. In the case of an incomplete fracture, it may be difficult to determine whether one or a plurality of fragments are included. In this case, the processing circuitry 1 executes the extracting function 13 to extract a bone suffering an incomplete fracture as a fragment region. The processing circuitry 1 executes the registration function 15 to register the extracted one fragment region with the bone region included in the target volume data. Depending on the registration result, the processing circuitry 1 may extract the bone suffering the incomplete fracture as a plurality of fragment regions, and register the plurality of extracted fragment regions with the bone region included in the target volume data. At this time, before performing registration of each fragment, the processing circuitry 1 acquires the surface shape of the fragment, and determines based on the acquired surface shape whether the fragment includes a portion suffering the incomplete fracture. This makes it possible to accurately arrange the fragment region even if the fragment region includes a crack such as a hairline fracture. Note that the processing circuitry 1 may be configured to accept, from the operator, designation of a region to be extracted as an independent fragment region for the bone suffering the incomplete fracture. The processing circuitry executes the extracting function 13 to process the designated region as a fragment region.

As described above, in this embodiment, the processing circuitry 1 determines the arrangement of the plurality of fragment regions included in the object volume data based on the shapes of the fragment regions and the shape of a bone region included in the target volume data. This allows the processing circuitry 1 to accurately register a plurality of rigid bodies, obtained by dividing one object, with the one original object.

Therefore, the medical image processing apparatus according to this embodiment can automatically create an image in which a bone fracture has been reduced. This eliminates the need for processing of performing manual registration of fragments, thereby lightening the load of the operator such as a doctor.

Furthermore, in this embodiment, the processing circuitry 1 sequentially performs registration of the fragment regions from the larger fragment region. This improves the registration accuracy.

In addition, in this embodiment, the processing circuitry 1 extracts fragment regions each having the preset size or more from the target volume data. This can efficiently perform registration of fragments which are to be treated.

In this embodiment, the processing circuitry 1 excludes a portion, with which the fragment region has been registered, of the bone region included in the target volume data from portions with which the fragment regions are to be registered. This can improve the registration accuracy while suppressing calculation processing by the processing circuitry 1.

In this embodiment, the processing circuitry 1 sets, in each fragment region, a boundary portion where a bone has been disconnected. Then, the processing circuitry 1 performs registration of the fragment region in consideration of the set boundary portion. This can arrange the fragment region in consideration of the portion where a bone fracture has occurred, thereby improving the registration accuracy.

Note that this embodiment has exemplified a case in which the processing circuitry 1 generates target volume data by performing mirror image reversal processing for data of a medical image including a healthy bone region, which has been generated by the modality. The present embodiment, however, is not limited to this. The storage 9 stores an artificially created model, for example, a standard dissecting chart related to a bone structure. The processing circuitry 1 which executes the data acquiring function 11 may be configured to acquire volume data associated with the standard dissecting chart from the storage 9, and generate target volume data from the acquired data.

The storage 9 stores volume data related to the subject before a disease such as a fracture occurs. That is, the storage 9 stores past volume data of the subject. More specifically, for example, if the subject has a left distal radius fracture, volume data which has been acquired for the healthy left hand before the subject gets the left distal radius fracture is set as past volume data. The processing circuitry 1 may execute the data acquiring function 11 to acquire the past volume data of the subject from the storage 9, and generate target volume data from the acquired data.

If, for example, the right and left bones have different sizes, the processing circuitry 1 may execute the data acquiring function 11 to enlarge or reduce the bone region included in the target volume data. More specifically, for example, after registration of the fragment region having the largest volume ends, the processing circuitry 1 compares the volume of the registered bone region with the volume of the registered fragment region. If the volume of the registered bone region is larger than the, volume of the registered fragment region by a preset value or more, the processing circuitry 1 reduces the volume of the bone region included in the target volume data. On the other hand, if the volume of the registered bone region is smaller than the volume of the registered fragment region by a preset value or more, the processing circuitry 1 enlarges the volume of the bone region included in the target volume data. The processing circuitry 1 may generate a plurality of target volume data by variously changing the enlargement/reduction magnification, register the fragment region with each of the target volume data, and select, as a registration object, the target volume data of the enlargement/reduction magnification having the highest degree of coincidence.

This embodiment has exemplified a case in which the processing circuitry 1 performs the segmentation processing for the object volume data including the bone fracture region in step S4. However, the present embodiment is not limited to this. The processing circuitry 1 may perform the segmentation processing for an object or range designated by the operator. At this time, the operator determines an object or range for which the segmentation processing is to be executed, with reference to the surface volume rendering image including the bone fracture region displayed on the display 3. This executes the segmentation processing for only the object or range designated by the operator. Thus, the processing of the processing circuitry 1 is suppressed, and the processing time taken to acquire the registration volume data is shortened.

A case in which the processing circuitry 1 executes the registration function 15 described in this embodiment to register the fragment regions with the bone region included in the target volume data in descending order of volumes or surface areas has been exemplified. The present embodiment, however, is not limited to this. The processing circuitry 1 may execute the registration function 15 to determine the registration order using elements other than the sizes such as the volumes of the fragment regions. More specifically, for example, the processing circuitry 1 execute the registration function 15 to select a fragment region which tends to be a mark at the time of registration, in other words, a fragment region having a characteristic shape.

Practical examples of the fragment region which tends to be a mark at the time of registration are a fragment region having a sharp-pointed shape obtained when a portion of the bone region is torn away, and a fragment region having a flat shape.

To select a fragment region which tends to be a mark at the time of registration, the processing circuitry 1 performs, for example, the following processing. That is, the processing circuitry 1 approximates a fitting curve representing the surface shape from the acquired information, and acquires, for example, feature amounts such as inflection points for defining smoothness based on the fitting curve. The processing circuitry 1 compares the feature amounts of the bone region included in the target volume data with the feature amounts of the fragment region for each region of about several cm, and sets, as a feature point, a region having almost equal feature amounts. The processing circuitry 1 acquires the feature points for the plurality of fragment regions, and selects, as the fragment region which tends to be a mark at the time of registration, the fragment region including the largest number of feature points. The processing circuitry 1 compares the selected fragment region with a predetermined portion in the bone region included in the target volume data, and calculates an evaluation value representing whether the shape of the selected fragment region is similar to that of the predetermined portion in the bone region. The processing circuitry 1 arranges the selected fragment region in a portion having the best calculated evaluation value. After registration of the selected fragment region ends, the processing circuitry 1 performs registration of the fragment region having the second largest number of feature points.

The processing circuitry 1 may determine the registration order based on a combination of the size such as the volume of the fragment region and other elements. More specifically, for example, the processing circuitry 1 executes the registration function 15 to sequentially perform registration of the fragment regions from the fragment region which has the largest size such as the largest volume and the largest number of feature points.

A case in which the processing circuitry 1 executes the rendering function 17 described in this embodiment to perform the rendering processing for the registration volume data has been exemplified. The present embodiment, however, is not limited to this. The processing circuitry 1 may execute the rendering function 17 to generate a surface volume rendering image by performing the rendering processing for the object volume data with which at least one fragment region has been registered. More specifically, for example, every time the fragment region is registered, the processing circuitry 1 may generate a surface volume rendering image by performing the rendering processing for the object volume data with which the fragment region has been registered. The processing circuitry 1 displays the generated surface volume rendering image on the display 3. At this time, the processing circuitry 1 may display the surface volume rendering image including the registered fragment region and the target surface volume rendering image side by side, or superimpose and display the surface volume rendering image including the registered fragment region on the target surface volume rendering image.

Figure 9:
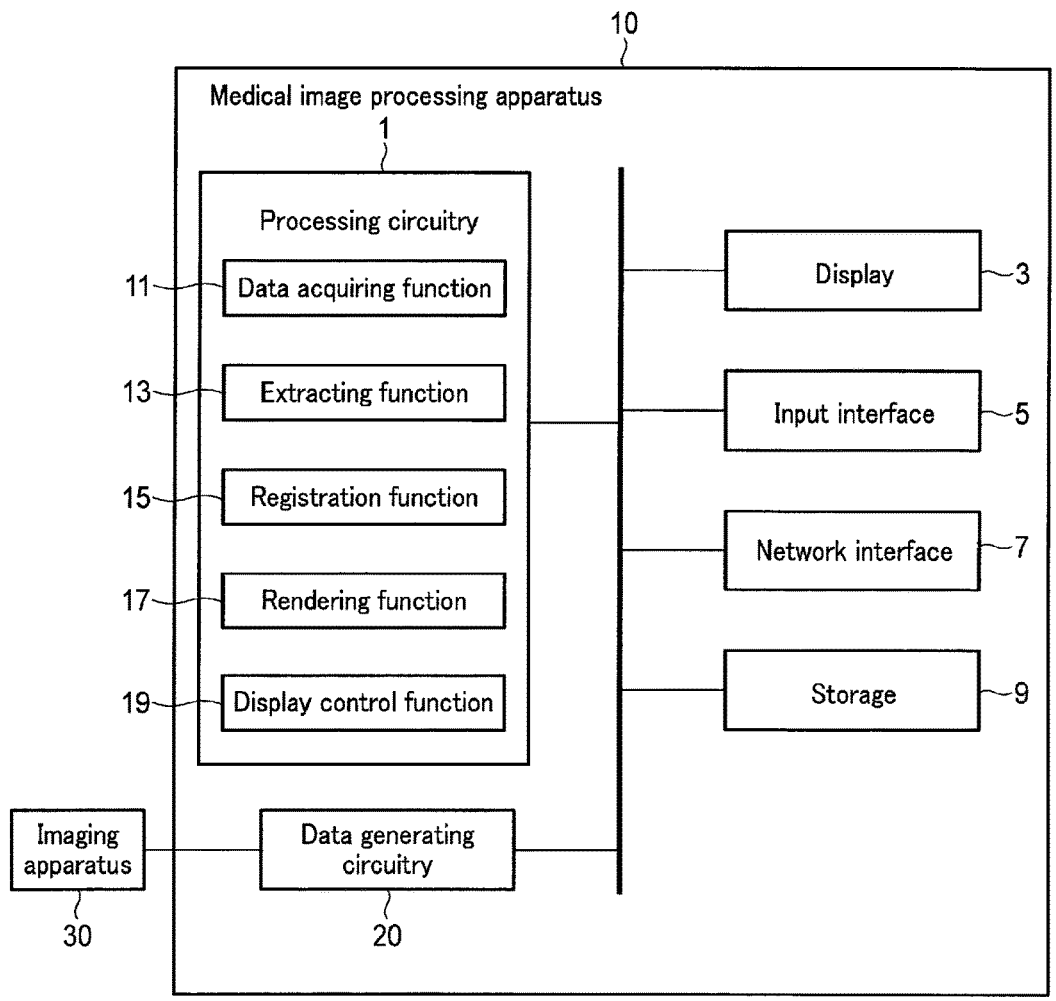
FIG. 9 is a block diagram showing the arrangement of a medical image diagnostic apparatus incorporating the medical image processing apparatus shown in FIG. 1.

Furthermore, the medical image processing apparatus according to this embodiment is incorporated in a modality such as an X-ray computed tomography apparatus, X-ray diagnostic apparatus, or magnetic resonance imaging apparatus, as shown in, for example, FIG. 9. FIG. 9 is a block diagram showing an example of the arrangement of a medical image diagnostic apparatus incorporating the medical image processing apparatus according to this embodiment. The medical image diagnostic apparatus shown in FIG. 9 includes a medical image processing apparatus 10 and an imaging apparatus 30. The imaging apparatus 30 is an apparatus which acquires raw data for generating an image of the interior of the subject in the medical image diagnostic apparatus such as an X-ray computed tomography apparatus, X-ray diagnostic apparatus, or magnetic resonance imaging apparatus. The medical image processing apparatus 10 includes data generating circuitry 20. The data generating circuitry 20 is a processor which generates object volume data including a bone fracture region and volume data including a healthy bone region based on the raw data acquired by the imaging apparatus 30. The volume data generated by the data generating circuitry 20 are stored in the storage 9.

The term "processor" used in the above description indicates, for example, a CPU (Central Processing Unit), a GPU (Graphics Processing Unit), or circuitry such as an ASIC (Application Specific Integrated Circuit) or a programmable logic device (for example, an SPLD (Simple Programmable Logic Device), CPLD (Complex Programmable Logic Device), or FPGA (Field Programmable Gate Array)). Note that the processing circuitry 1 may be configured to directly incorporate the image processing program in the circuitry of the processor, instead of saving the program in the storage 9. In this case, the processor implements the function by reading out and executing the program incorporated in the circuitry. Note that the processor according to this embodiment may implement the function by combining a plurality of individual circuitry without limitation to a case in which the processor is formed as a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus comprising:
processing circuitry configured to
acquire object volume data including a bone fracture region acquired from a subject and target volume data acquired based on a healthy bone region corresponding to the bone fracture region,
extract a plurality of fragment regions from the object volume data, and
arrange the plurality of extracted fragment regions in the object volume data based on shapes of the plurality of fragment regions and a shape of a bone region included in the target volume data; and
a display that displays an image based on the object volume data in which the fragment regions are arranged.

2. The medical image processing apparatus of claim 1, wherein the processing circuitry sequentially arranges the plurality of extracted fragment regions from a larger fragment region.

3. The medical image processing apparatus of claim 1, wherein the processing circuitry sequentially arranges the plurality of extracted fragment regions from a fragment region having a characteristic shape.

4. The medical image processing apparatus of claim 1, wherein the processing circuitry extracts fragment regions each having a size not smaller than a predetermined size from the object volume data.

5. The medical image processing apparatus of claim 1, wherein the processing circuitry arranges the extracted fragment region by sequentially registering the extracted fragment region with the bone region included in the target volume data, and excludes a portion of the bone region, with which the fragment region has been registered, from portions with which the fragment regions are to be registered.

6. The medical image processing apparatus of claim 1, wherein the processing circuitry sets, in the extracted fragment region, a boundary portion where a bone has been disconnected, and arranges the plurality of extracted fragment regions in consideration of the set boundary portion.

7. The medical image processing apparatus of claim 1, wherein the processing circuitry acquires the target volume data by performing mirror image reversal processing for the volume data including the healthy bone region, which is acquired from the same subject as the subject from which the object volume data has been acquired.

8. The medical image processing apparatus of claim 1, wherein the processing circuitry acquires the target volume data based on an artificially created model.

9. The medical image processing apparatus of claim 1, wherein the processing circuitry acquires the target volume data based on volume data acquired in the past for the same subject as the subject from which the object volume data has been acquired.

10. The medical image processing apparatus of claim 1, wherein the processing circuitry changes a color of at least one fragment included in the image.

11. The medical image processing apparatus of claim 10, wherein the processing circuitry switches whether to change the color of at least one fragment included in the image.

12. The medical image processing apparatus of claim 1, wherein the processing circuitry changes opacity of at least one fragment included in the image.

13. The medical image processing apparatus of claim 12, wherein the processing circuitry switches whether to change the opacity of at least one fragment included in the image.

14. The medical image processing apparatus of claim 1, wherein the processing circuitry displays, on the display, a boundary line between fragments included in the image.

15. The medical image processing apparatus of claim 14, wherein the processing circuitry switches whether to display, on the display, the boundary line between the fragments included in the image.

16. A medical image diagnostic apparatus comprising:
an imaging apparatus configured to acquire data for generating an image of a bone of a subject;
data generating circuitry configured to generate object volume data including a bone fracture region based on the data;
processing circuitry configured to
acquire target volume data based on a healthy bone region corresponding to the bone fracture region,
extract a plurality of fragment regions from the object volume data, and
arrange the plurality of extracted fragment regions in the object volume data based on shapes of the plurality of fragment regions and a shape of a bone region included in the target volume data; and
a display that displays an image based on the object volume data in which the fragment regions are arranged.

17. A method for image processing, the method comprising:
acquiring object volume data including a bone fracture region acquired from a subject;
acquiring target volume data based on a healthy bone region corresponding to the bone fracture region;
extracting a plurality of fragment regions from the object volume data;
arranging the plurality of extracted fragment regions in the object volume data based on shapes of the plurality of fragment regions and a shape of a bone region included in the target volume data; and
displaying an image based on the object volume data in which the fragment regions are arranged.

* * * * *